(12) United States Patent
Mielekamp et al.

(10) Patent No.: US 8,798,339 B2
(45) Date of Patent: Aug. 5, 2014

(54) TARGETING METHOD, TARGETING DEVICE, COMPUTER READABLE MEDIUM AND PROGRAM ELEMENT

(75) Inventors: Pieter Maria Mielekamp, Veldhoven (NL); Robert Johannes Frederik Homan, Batenburg (NL); Drazenko Babic, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 789 days.

(21) Appl. No.: 12/599,514

(22) PCT Filed: May 5, 2008

(86) PCT No.: PCT/IB2008/051722
§ 371 (c)(1),
(2), (4) Date: Nov. 10, 2009

(87) PCT Pub. No.: WO2008/139354
PCT Pub. Date: Nov. 20, 2008

(65) Prior Publication Data
US 2010/0215213 A1 Aug. 26, 2010

(30) Foreign Application Priority Data

May 10, 2007 (EP) .................................. 07107957

(51) Int. Cl.
*G06K 9/00* (2006.01)
(52) U.S. Cl.
USPC .......................................... 382/128; 600/427
(58) Field of Classification Search
CPC ............................ G06T 7/0012; G06F 19/321
USPC ............. 382/128–134; 600/424; 38/128–134
See application file for complete search history.

(56) References Cited

U.S. PATENT DOCUMENTS 5,799,055 A 8/1998 Peshkin et al.
6,505,065 B1 * 1/2003 Yanof et al. ................... 600/427
(Continued)

FOREIGN PATENT DOCUMENTS

EP 1095628 A2 5/2001
EP 1103229 A2 5/2001
(Continued)

OTHER PUBLICATIONS

Gering et al., An Integrated Visualization System for Surgical Planning and Guidance Using Image Fusion and an Open MR. Journal of Magnetic Resonance Imaging, 13:967-975 (2001).*

*Primary Examiner* — Mark Holcomb
*Assistant Examiner* — Jonathan K Ng (57) ABSTRACT

This invention will introduce a fast and effective target approach planning method preferably for needle guided percutaneous interventions using a rotational X-ray device. According to an exemplary embodiment A targeting method for targeting a first object in an object under examination is provided, wherein the method comprises selecting a first two-dimensional image of an three-dimensional data volume representing the object under examination, determining a target point in the first two-dimensional image, displaying an image of the three-dimensional data volume with the selected target point. Furthermore, the method comprises positioning the said image of the three-dimensional data volume by scrolling and/or rotating such that a suitable path of approach crossing the target point has a first direction parallel to an actual viewing direction of the said image of the three-dimensional data volume and generating a second two-dimensional image out of the three-dimensional data volume, wherein a normal of the plane of the second two-dimensional image is oriented parallel to the first direction and crosses the target point.

23 Claims, 6 Drawing Sheets

(56) References Cited

U.S. PATENT DOCUMENTS

| | | | |
|---|---|---|---|
| 6,610,013 B1* | 8/2003 | Fenster et al. | 600/439 |
| 6,671,538 B1* | 12/2003 | Ehnholm et al. | 600/425 |
| 7,343,195 B2* | 3/2008 | Strommer et al. | 600/424 |
| 7,518,619 B2* | 4/2009 | Stoval et al. | 345/619 |
| 2002/0156375 A1* | 10/2002 | Kessman et al. | 600/439 |
| 2003/0073901 A1* | 4/2003 | Simon et al. | 600/424 |
| 2005/0015005 A1 | 1/2005 | Kockro | |
| 2006/0025679 A1* | 2/2006 | Viswanathan et al. | 600/424 |
| 2006/0064010 A1 | 3/2006 | Cannon, Jr. et al. | |
| 2006/0215812 A1 | 9/2006 | Ostermeier | |
| 2007/0244387 A1* | 10/2007 | Rodriguez Ponce et al. | 600/411 |
| 2008/0123922 A1* | 5/2008 | Gielen et al. | 382/131 |
| 2010/0036384 A1* | 2/2010 | Gorek et al. | 606/104 |
| 2010/0114094 A1* | 5/2010 | Thapliyal et al. | 606/41 |

FOREIGN PATENT DOCUMENTS

| | | |
|---|---|---|
| EP | 1571581 A1 | 9/2005 |
| WO | 03045264 A1 | 6/2003 |
| WO | 2005119505 A2 | 12/2005 |

* cited by examiner

TARGETING METHOD, TARGETING DEVICE, COMPUTER READABLE MEDIUM AND PROGRAM ELEMENT

FIELD OF INVENTION

The invention relates to a targeting method, a targeting device, a system, a computer readable medium and a program element, in particular to a method for targeting a first object in an object under examination.

TECHNICAL BACKGROUND

An important class of image guided interventional procedures are the so-called needle guided percutaneous interventions. The clinical procedures of interest are all needle guided embolisation, biopsies and ablation procedures in the domain of: vertrebroplasty, kyphoplasty, neuro biopsies in neoplastic cranial disease and percutaneous rhizotomy in trigeminal neuralgia.

Two of the most frequently used imaging techniques for the image guidance are ultrasonic (US) based and computer tomography (CT) based. The US guided procedures are characterized by an interactive needle advancement monitoring and relatively good real time visualization of anatomical soft tissue structures. However, this technique suffers from multiple drawbacks, relatively poor visualization of bony structures filled with air, poor visibility when bony anatomy is superimposed on the structure of interest, low signal quality in obese patients (subcutaneous fat), for example. The CT guided interventions provide high contrast resolution distortion-less images and good visualization of the anatomical structures. The disadvantage of the technique is poor patient access and room sterility issues. An intervention room equipped with a rotational X-ray device is much more suitable for such procedures, but for most of the procedures the contrast resolution of the X-ray device is not sufficient.

It is known from US2006/0215812, that preparations can be made for a puncture intervention using images obtained from Magneto-Resonance/Computer Tomography and rotational X-ray devices. Here as part of these preparations the target and start/entry points for the puncture have to be defined in the three-dimensional-volume set by indicating them in mutually orthogonal cross sectional slices. The problem with this process is that a tedious trial and error method must be followed to define/evaluate the resulting needle trajectory in the cross-sectional slices. In the context of rotational X-ray, this process is hindered by the fact that sometimes the actual entry point is difficult to locate because the skin may not always be visible within the reconstructed region of interest.

Furthermore usually some global constraints must be fulfilled, such as entering a cavity or avoiding or passing in between bone or vessel material that is sometimes difficult to evaluate on cross sectional slices.

Because the puncture preparations are performed just before the intervention i.e. directly after the rotational scan with a patient (who is not supposed to move) on the table, it is important that a fast and effective trajectory plan is available/obtained.

SUMMARY OF THE INVENTION

It may be desirable to provide an efficient targeting method, a targeting device, a system, a computer readable medium and a program element usable in a targeting device. Thus, it is one intention of the present invention to present a simple, fast and effective targeting method, preferably, to approach a planning/preparation method for needle guided percutaneous interventions using C-arm based X-ray devices.

This need may be met by a targeting method, a targeting device, a system, a computer readable medium and a program element according to the independent claims.

In the following, further exemplary embodiments of the targeting method will be described. However, these embodiments apply also for the targeting device, the system, the computer readable medium and the program element.

According to claim 1 of the present invention a targeting method for targeting a first object in an object under examination is provided. The method comprises, selecting a first two-dimensional image, e.g. a slice or slab, of an three-dimensional data volume representing the object under examination, determining a target point in the first two-dimensional image, displaying an image of the three-dimensional data volume with the selected target point and positioning the said image of the three-dimensional data volume by scrolling and/or rotating such that a suitable path of approach, e.g. crossing the target point has a first direction parallel to an actual viewing direction of the said image of the three-dimensional data volume. Furthermore, the method comprises, generating a second two-dimensional image out of the three-dimensional data volume, wherein a normal of the plane of the second two-dimensional image is oriented parallel to the first direction and crosses the target point.

According to a preferred embodiment of the invention, in first step of the method, an axial (feet to head) cross-sectional view, selected by default from a three-dimensional-data volume is presented to the user as the said first two-dimensional image. The first two-dimensional image may be generated via Multi Plane Reconstruction (MPR) slice rendering of a user controllable slab.

By browsing through cross-sectional slices, the user of the method is able to localise and determine a target point for a first object, e.g. a needle. The slices may be orientated orthogonal to the axial view.

Once the target point has been found a suitable path of approach for an intended needle trajectory must be specified, for instance by indication of a second point, e.g. an entry point into the object under examination or by means of a line drawn from the target to a point somewhere outside the object of examination.

For a suitable path of approach in general an oblique slice will be needed. By means of a combination of scrolling and rotation of the three-dimensional-volume slice the required target approach may be selected.

According to a further embodiment of the present invention, by using the target as centre of rotation, the target will be fixed during the rotations. Once the correct oblique slice has been found, the approach of the needle in the selected plane can be defined.

In general some global constrains may be fulfilled during targeting method operation, such as entering a cavity with a needle or avoiding or passing in between bone or vessel material with the needle that may be difficult to evaluate using cross sectional slices.

Thus, according to an embodiment invention it is proposed to start with an overall volume/gradient rendered presentation, with the correct setting of a known soft tissue transfer function. By means of three-dimensional rotation, the volume can now be positioned in such a way, that a bull's-eye view on a suitable path of approach, with the viewing direction coinciding with this path, is obtained. By a simple indication of the centre of the bull's-eye path the corresponding oblique cross sectional slice that is orthogonal to line of sight, can be generated as the second two-dimensional image and presented to the user in a normalized (axial) orientation, i.e. with zero rotation around the (axial) viewing direction.

This may be preferably effectuated by automatically switching to a MPR slice rendering with a corresponding soft tissue transfer function. In the second two-dimensional image the optimal path of approach of a needle is represented as an infinite line, passing at both ends through the volume boundaries. The needle trajectory can now be specified along this line.

By toggling between the MPR slice and the three-dimensional volume presentations, the planned trajectory can be visualised and checked by means of a three-dimensional needle graphics representation, in both the local soft tissue and the global volume rendered presentations.

A problem with the method as lined out above is that in general the (soft tissue) targets are not visible in the volume rendered visualization, which may limits the applicability.

The solution that is proposed is to first locate and identify the target in the axial cross sectional slice. The target(s) can be located, positioned in current plane and be represented by means of a simple three-dimensional graphical object, like a small sphere. By using this three-dimensional model based representation the target(s) can be visualised at the correct three-dimensional position in the volume rendered presentation. In this presentation the optimal approach can now by defined using the bull's eye approach using this three-dimensional representation of the target(s).

It will be clear that the marking of the target(s) based on soft tissue information is not restricted to actual targets as such but may be extended to general marking of clinically interesting (soft-tissue) regions, that must be avoided or reached. In which case it may be advantageous to use some colour coding and tag some geometrical dimensions to these regions.

By assuring a minimum amount of visibility the current needle path and targets/clinical regions will always be visible with the various three-dimensional volume rending modes and densities.

Furthermore to invalidate the visibles like current needle trajectory and clinical regions they be made semi transparent if there are not in their definition plane due the scrolling and rotation operations during the slice rendering presentation.

By means of generally known three-dimensional/three-dimensional registration the planning method as described above may also be applied on the bases of overlaid pre-interventional soft-tissue volumes obtained from other modalities like CT and MR, possibly combined with contrast injection for vessel visualisation during the rotation scan.

According to a further embodiment of the present invention, a targeting device for targeting a first object in an object under examination is provided. The targeting device comprises a selecting unit adapted to select a first two-dimensional image of an three-dimensional data volume representing the object under examination, a determining adapted to determine a target point in the first two-dimensional image, a displaying unit adapted to display an image of the three-dimensional data volume with the selected target point, a positioning unit adapted to position the said image of the three-dimensional data volume by scrolling and/or rotating such that a suitable path of approach crossing the target point has a first direction parallel to an actual viewing direction of the said image of the three-dimensional data volume and a generating unit adapted to generate a second two-dimensional image out of the three-dimensional data volume, wherein a normal of the plane of the second two-dimensional image is oriented parallel to the first direction and crosses the target point.

According to a further embodiment of the present invention, a system for targeting a first object in an object under examination is provided. The system comprises a radiation source, a radiation detector and a targeting device according to the aforesaid embodiment. The radiation detector is adapted to record the data representing the three-dimensional data volume.

The system further comprises a computer tomography apparatus which is adapted to generate the two-dimensional images of the object under examination.

According to a further embodiment of the present invention, a computer readable medium is provided in which a program for targeting a first object in an object under examination is stored, which program, when executed by a processor, is adapted to control a method comprises, selecting a first two-dimensional image of an three-dimensional data volume representing the object under examination, determining a target point in the first two-dimensional image, displaying an image of the three-dimensional data volume with the selected target point, positioning the said image of the three-dimensional data volume by scrolling and/or rotating such that a suitable path of approach crossing the target point has a first direction parallel to an actual viewing direction of the said image of the three-dimensional data volume and generating a second two-dimensional image out of the three-dimensional data volume, wherein a normal of the plane of the second two-dimensional image is oriented parallel to the first direction and crosses the target point.

According to a further embodiment of the present invention a program element for targeting a first object in an object under examination is provided. The program, when executed by a processor, is adapted to control a method comprises, selecting a first two-dimensional image of an three-dimensional data volume representing the object under examination, determining a target point in the first two-dimensional image, displaying an image of the three-dimensional data volume with the selected target point, positioning the said image of the three-dimensional data volume by scrolling and/or rotating such that a suitable path of approach crossing the target point has a first direction parallel to an actual viewing direction of the said image of the three-dimensional data volume, and generating a second two-dimensional image out of the three-dimensional data volume, wherein a normal of the plane of the second two-dimensional image is oriented parallel to the first direction and crosses the target point.

According to a further embodiment of the invention, the target point is used as the center of rotation during the positioning step.

According to a further embodiment of the invention, the targeting method further comprises, generating a third two-dimensional image out of the three-dimensional data volume, wherein the plane of the third two-dimensional image is oriented parallel to the first direction and crosses the target point.

According to a further embodiment of the invention, the two-dimensional images are selected as slices of the three-dimensional data volume of the object under examination.

According to a further embodiment of the invention, the path of approach is the path of an intended needle trajectory trough the object under examination.

According to a further embodiment of the invention, the targeting further comprises, determining an entry point of the path of approach into the object under examination.

According to a further embodiment of the invention, the targeting method according to anyone of the preceding claims, further comprises, projecting the path of approach, the entry point and/or the target point by a graphical object onto at least one of the said images.

According to a further embodiment of the invention, the graphical object representing the path of approach is a line or a three dimensional object, preferably a needle.

According to a further embodiment of the invention, the graphical object representing the target point is a sphere or a cross-hair.

According to a further embodiment of the invention, the first two-dimensional image is an cross-sectional view of the object under examination.

According to a further embodiment of the invention, the selection of the third two-dimensional image is caused by manually clicking on the graphical object representing the target point.

According to a further embodiment of the invention, the targeting method further comprises, toggling between at least two of the said images comprising graphical objects, preferably between the third two-dimensional image and the second two-dimensional image and/or the image of the three-dimensional data volume.

According to a further embodiment of the invention, the targeting method according to anyone of the preceding claims, further comprising, displaying at least one, preferably two of the said images comprising graphical objects to the user in a predefined orientation.

According to a further embodiment of the invention, the object under examination is a patient, and the predefined orientation of said images is an axial (feet to head) multi planar reformat (MPR) rendered cross section out of a 3D reconstructed data volume, preferably with no rotation angle around a perpendicular (viewing direction) of the plane of said images.

According to a further embodiment of the invention, regions of interest in the object under examination and/or the graphical objects are coloured.

According to a further embodiment of the invention, at least portions of the coloured regions of interest in the object under examination and/or at least portions of the graphical objects which extend apart from the plane of the third two-dimensional image rendered semi-transparent.

According to a further embodiment of the invention, the three-dimensional image is reconstructed out of the three-dimensional data volume recorded by a computer tomography apparatus.

According to a further embodiment of the invention, the three-dimensional image is recorded by a C-arm device.

According to a further embodiment of the invention, the targeting method further comprises, generating a graphic, showing the planned path and the target point, from a three-dimensional graphical model, and overlaying the graphic on at least one of the two-dimensional images of the object under examination.

According to a further embodiment of the invention, the said graphic comprises a scale.

According to a further embodiment of the invention, the targeting method further comprises, rendering the graphic, the image of the three-dimensional data volume and the two-dimensional under the same perspective.

The said path of approach represents a first direction from which a second direction can be derived in which second direction a consecutive second image can be taken or recorded. The second image is generally a two-dimensional image which normal is parallel with the first direction, i.e. image is recorded in the direction of the determined path.

In this application the term "an image" relates to the actual image as well as to the recorded data from which, by using well known methods, the actual image can be reconstructed. This targeting method may be usable in the field of C-arm apparatuses and/or tomography apparatuses, e.g. a computed tomography apparatus. Preferably, the images are fluoroscopic images, i.e. the data representing the fluoroscopic images, are taken by using a C-arm apparatus.

According to another exemplary embodiment of the targeting method the two-dimensional image is selected as a slice of a three-dimensional image of the object under examination. Preferably, the three-dimensional image is reconstructed out of data recorded by a computer tomography apparatus. Depending on the application three-dimensional (three-dimensional) data can be acquired with a CT modality (apparatus), e.g. depending on contrast resolution or if diagnostic data is already present, MR modality (apparatus) or with a C-arm with which CT-like image quality can be reached depending on the number of images acquired during a rotational scan.

Using a three-dimensional image, e.g. a voxel representation, of a three-dimensional object as an initial image from which a two-dimensional image is selected, is an efficient way to ensure that at least one slice or slab of the three-dimensional image contains the target point. The voxel representation can be efficiently reconstructed out of data recorded in a computer tomography (CT) with well known methods of reconstruction.

According to the invention, the determination of the two-dimensional images can be done by indicating within a three-dimensional volume of the object under examination a target point. The three-dimensional volume can be from a different modality or can be acquired ob the same modality with a rotational scan. For effective path planning it may furthermore be advantageous, in order to prevent vessel perforation, to perform the planning on a fused volume presentation where the CT-(like) oblique volume slab is combined with a three-dimensional angiographic volume rendering of the same object. The relation between the volume data and the fluoroscopic images can, for example, be determined with a machine based registration method whereby a C-arm geometry is calibrated. If the three-dimensional volume data is originating from a different modality the relation may, for example, be determined with a registration method.

In one aspect of the invention from the planned path a three-dimensional graphical model is generated, which is visible inside the volume data. With the determined geometrical relation between the images and the volume data the C-arm can be moved to the optimal entry point view and progression point view on base of the three-dimensional graphical model, taking into account the bending of the C-arm and the perspective nature of the images, wherein the calculations are done from volume coordinates to C-arm sensor coordinates. For each position of the C-arm the three-dimensional graphical model of the planned path can be projected as a 2D graphic onto the fluoroscopic image. The position/shape of the object visible on the images must be the same as the projected graphic, during insertion into the body to keep on the planned path. Furthermore the volume data inside the slice/slab containing the planned path can also be projected onto the images. This way the surrounding structures around the planned path and the target are made visible. The contrast resolution of the images may not good enough to see the soft tissue structures and the target structure or structures are only visible with contrast agents.

According to another exemplary embodiment the targeting method further comprises, projecting a three-dimensional graphical model onto the images. In other words, the three-dimensional graphical model may be projected onto the images. This three-dimensional graphical model can be generated from the planned path. If the C-arm orientation is equal to the entry point orientation the three-dimensional graphical model be projected as a circle or a cross-hair. Preferably, the image can be a so-called live image, e.g. an image which is continuously or at least repeatedly recorded.

In this context a graphic may mean a simplified image. Such a graphic can be easily overlaid on the two-dimensional image while still showing a sufficient contrast to be seen in this overlaying mode. Thus, it might be possible to display the target point on the overlaid image even in case in the image the first object or the target point is only depicted showing low contrast. The implementing of a scale in the graphic may be an efficient way to measure and/or to control the advancing of the first object in the second image. Alternatively, the target point may be added into the two-dimensional, i.e. the two-dimensional image may be altered by introducing the target point as a structure. This might be advantageous in case the target point is represented by a structure having low contrast in the image.

According to another exemplary embodiment the targeting method further comprises rendering the graphic and the fluoroscopic image under the same perspective. In particular, all rendering may be done with the same (inverse) perspective as present in the live fluoro images.

The rendering of the slices, volumes and/or graphics may be done with the same perspective as the corresponding images in order to achieve an improved tracking of the first object, e.g. a needle, in the object under examination. This may an efficient way to improve the targeting method by overcome a problem which might occur due to the fact that a first object, e.g. a needle, will be projected as a circle if the needle is pointed towards a focus position of the device used for taking the fluoroscopic images instead of the towards the endpoint (target point) of the planned path due to the perspective nature of the fluoroscopic images. This problem may be prevented by adapting the rotation of the C-arm in such a way that the focus position lays on the extension of the planned path line. That is, due to the perspective nature of the fluoroscopic images the object will not be projected as a circle if the detector plane is equal to the orthogonal plane of the planned path, to correct for this the orientation of the C-arm may be adapted in such a way that the focus point (e.g. X-ray source) is placed on the extension of the planned path, wherein the calculations are done from the volume coordinates to C-arm sensor coordinates.

It should be noted in this context, that the present invention is not limited to a C-arm based image and/or computed tomography, but may include the use of C-arm based three-dimensional rotational X-ray imaging, magnetic resonance imaging, positron emission tomography or the like. In particular, the volume data used for the planning may be originating from all kinds of modalities as long as the data can be registered to the modality used for the intervention. It should also be noted that this technique may in particular be useful for medical imaging and medical targeting like targeting a needle to a predetermined target point on or in the body of a patient.

A method according to an exemplary embodiment of the invention may have the advantages that an entrance point (puncturing spot) into a body as well as an entrance angle into the body may be determinable during a medical procedure. Further, the needle position in the body may be determinable during the procedure and shutter positions may be set to reduce the patient dose during a CT acquisitions to monitor the progress of the procedure.

These and other aspects of the present invention will become apparent from and elucidated with reference to the embodiment described hereinafter.

BRIEF DESCRIPTION OF THE DRAWINGS

Exemplary embodiments of the present invention will be described in the following, with reference to the following drawings.

DETAILED DESCRIPTION OF AN EXEMPLARY EMBODIMENT

The illustration in the drawings is schematically. In different drawings, similar or identical elements are provided with the similar or identical reference signs.

Figure 1:
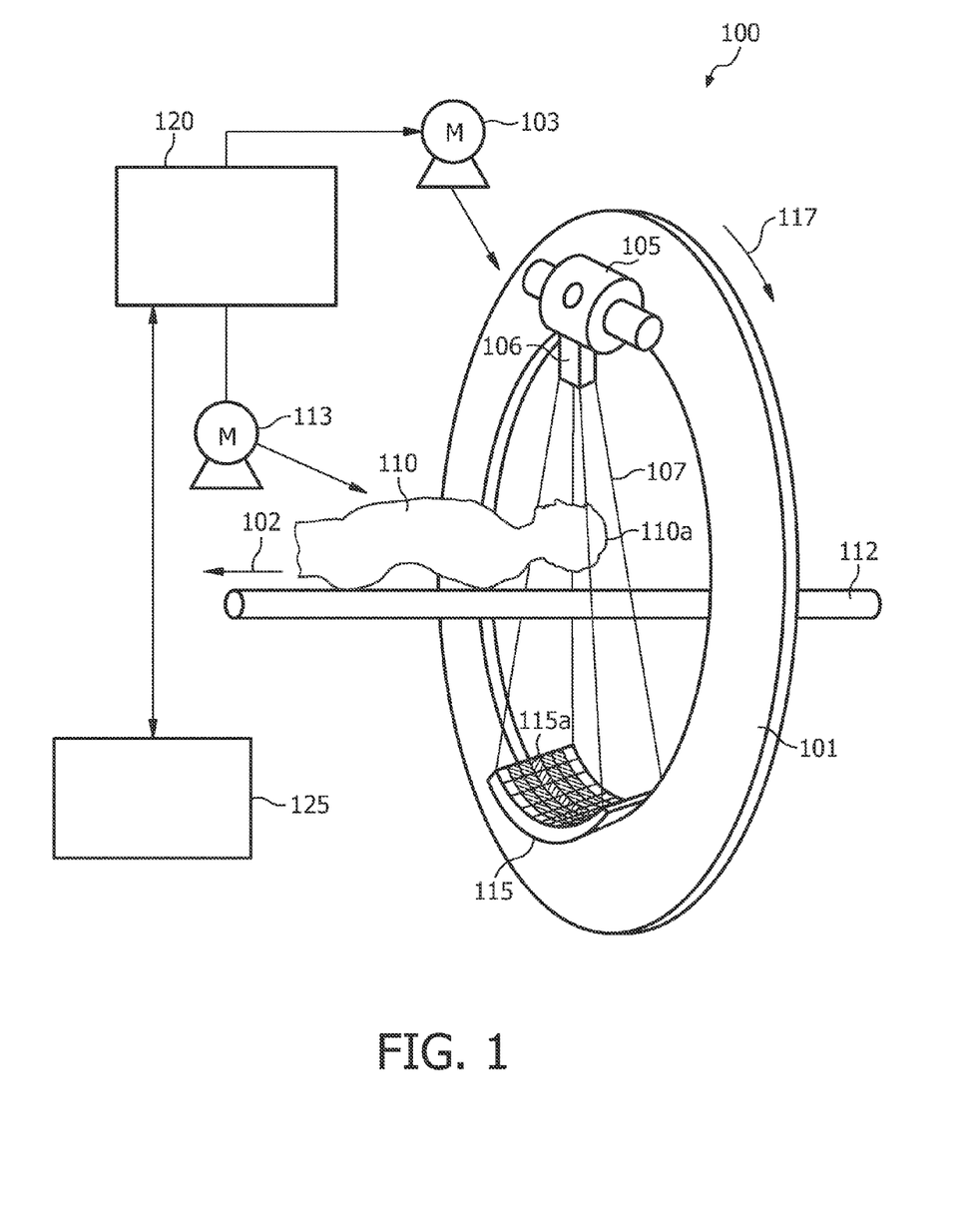
FIG. 1 shows a simplified schematic representation of a computed tomography system.

FIG. 1 shows an exemplary embodiment of a computed tomography scanner system which can be used in order to provide a three-dimensional image from which a slice can be selected. For the further targeting method a so-called C-arm device can be used which looks similar to the CT but comprises only a C-arm gantry, i.e. a gantry in form of a C, instead of a gantry, which is depicted in FIG. 1.

The computed tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 105 designates a source of radiation such as an X-ray source, which emits polychromatic or monochromatic radiation.

Reference numeral 106 designates an aperture system which forms the radiation beam emitted from the radiation source unit to a cone-shaped radiation beam 107. The cone-beam 107 is directed such that it penetrates an object of interest 110 arranged in the center of the gantry 101, i.e. in an examination region of the CT scanner, and impinges onto the detector 115 (detection unit). As may be taken from FIG. 1, the detector 115 is arranged on the gantry 101 opposite to the radiation source unit 105, such that the surface of the detector 115 is covered by the cone beam 107. The detector 115 depicted in FIG. 1 comprises a plurality of detection elements 115a each capable of detecting X-rays which have been scattered by, attenuated by or passed through the object of interest 110. The detector 115 schematically shown in FIG. 1 is a two-dimensional detector, i.e. the individual detector elements are arranged in a plane, such detectors are used in so called cone-beam tomography.

During scanning the object of interest 110, the radiation source unit 105, the aperture system 106 and the detector 115 are rotated along the gantry 101 in the direction indicated by an arrow 117. For rotation of the gantry 101 with the radiation source unit 105, the aperture system 106 and the detector 115, the motor 103 is connected to a motor control unit 120, which is connected to a control unit 125. The control unit might also be denoted and used as a calculation, reconstruction or determination unit and can be realized by a computer.

In FIG. 1, the object of interest 110 is a human being which is disposed on an operation table 112. During the scan of a head 110a, a heart, a lung or any other part of the human being 110, while the gantry 101 rotates around the human being 110, the operation table 112 may displace the human being 110 along a direction parallel to the rotational axis 102 of the gantry 101. This may be done using a motor 113. By this, the heart is scanned along a helical scan path. The operation table 112 may also be stopped during the scans to thereby measure signal slices.

The detector 115 is connected to the control unit 125. The control unit 125 receives the detection result, i.e. the read-outs from the detection elements 115a of the detector 115 and determines a scanning result on the basis of these read-outs. Furthermore, the control unit 125 communicates with the motor control unit 120 in order to coordinate the movement of the gantry 101 with motors 103 and 113 with the operation table 112.

The control unit 125 may be adapted for reconstructing an image from read-outs of the detector 115. A reconstructed image generated by the control unit 125 may be output to a display (not shown in FIG. 1) via an interface.

The control unit 125 may be realized by a data processor to process read-outs from the detector elements 115a of the detector 115.

Figure 2:
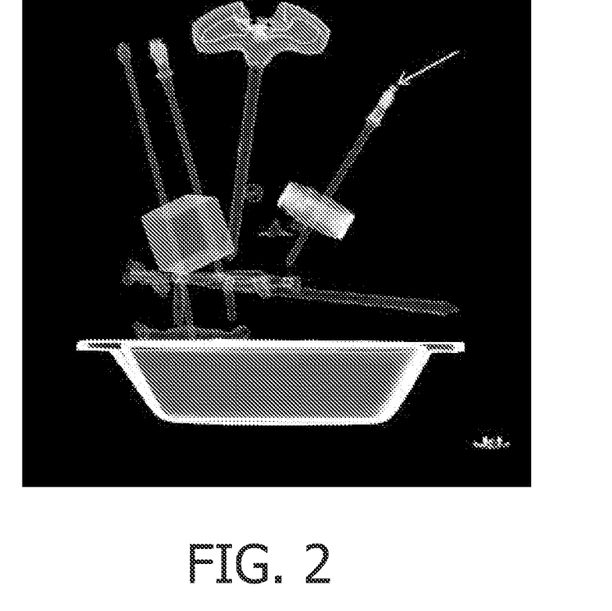
FIG. 2 shows a phantom of a number of objects, particularly a needle, wrapped in a textile.

The method as described above will be illustrated by means of a phantom as shown in FIG. 2. In this phantom, as shown in a gradient rendered visualization, a number of objects have been wrapped up in a textile. Through the textile a number of randomly oriented needles have been inserted. Now the goal is to define an approach along the path of a needle, indicated by an arrow.

Figure 3:
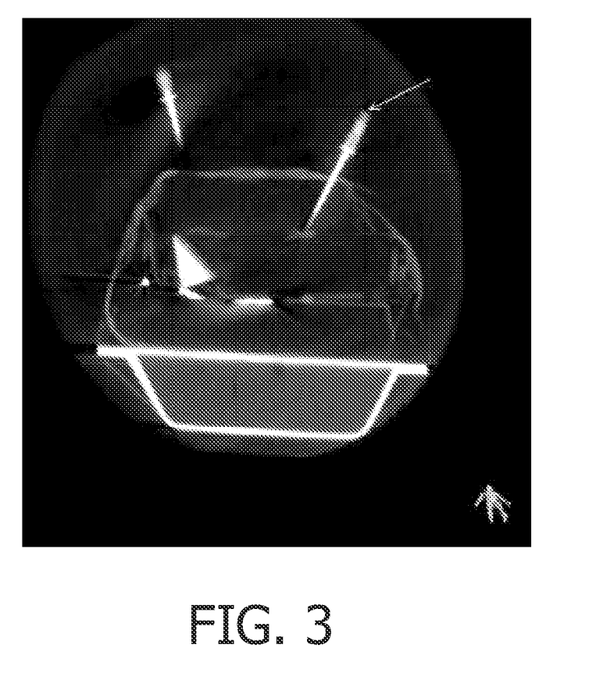
FIG. 3 shows an axial slice such that the needle is visible completely.

FIG. 3 shows the axial slice that is on its way to be manually oriented in this cross sectional plane such that indicated needle is visible.

Figure 4:
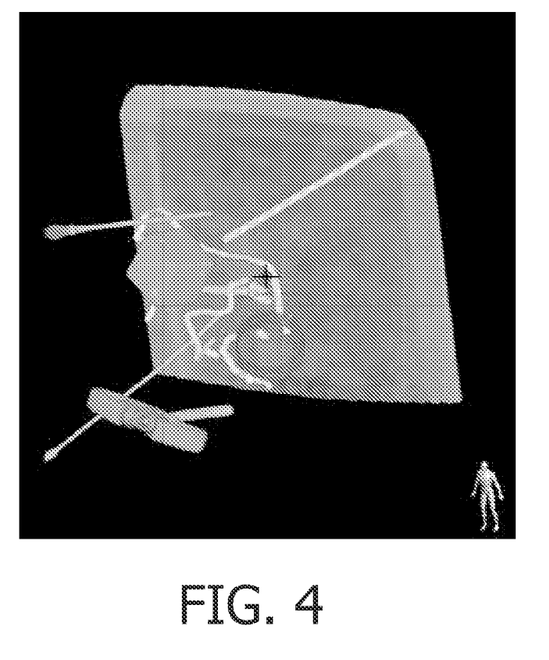
FIG. 4 shows the indicated needle as a graphical object in a so-called bulls-eye view.
Figure 5:
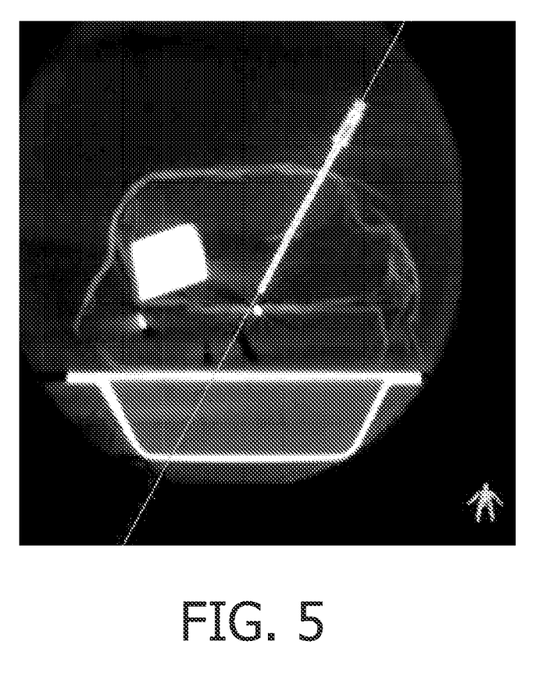
FIG. 5 shows the resulting slab orientation of that is obtained by clicking on this projected target in the cross hair of FIG. 4.

FIG. 4 shows the much simpler interaction where the indicated needle is projected as a dot. The target point is indicated by a cross-hair FIG. 5 shows the resulting slab orientation that is obtained by clicking on this projected target in the cross hair of FIG. 4. In this figure the resulting normalised axially orientation (with horizontal table position) with the path of approach indicated as an infinite line is shown.

Figure 6:
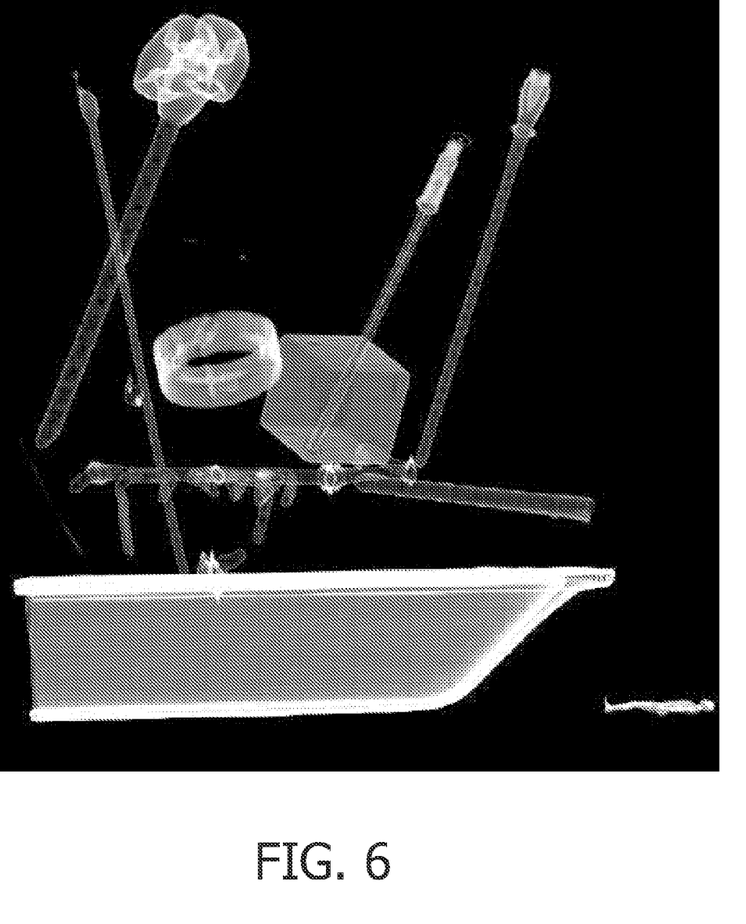
FIG. 6 shows a gradient rendered volume after indication of a begin/end point along the line of FIG. 5 with a three-dimensional model of the needle.

After indication of the begin/end point along this line, the 3D needle model is shown in the gradient rendered volume presentation shown in FIG. 6.

Figure 7:
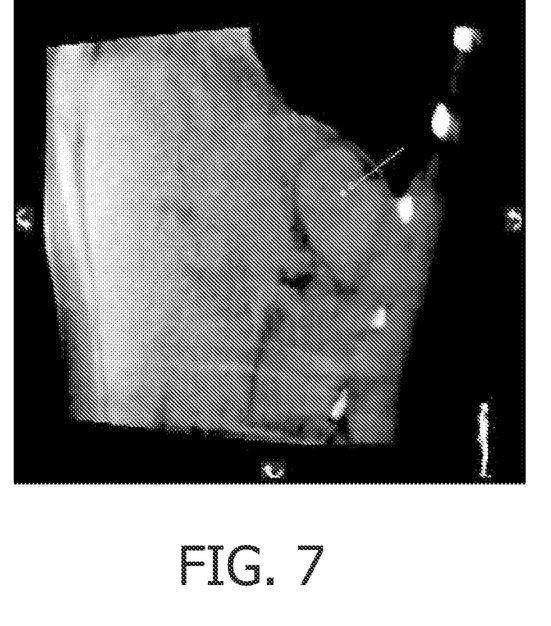
FIG. 7 shows a fluoroscopic image of a clinical case in which a kidney cyst is marked in a soft tissue sectional slice.

FIG. 7 shows a clinical case in which a kidney cyst is marked in a soft tissue cross-sectional slice. In particular, FIG. 7 corresponds to FIG. 3. A target point is indicated by an arrow.

Figure 8:
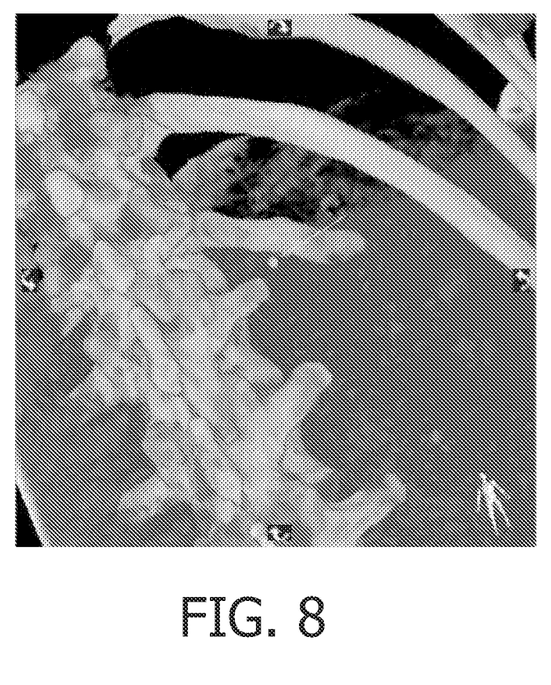
FIG. 8 shows a 3D volume rendered bull's eye view on the target.

FIG. 8 shows a 3D volume rendered bull's eye view on the target that provides the correct clearance. In particular, FIG. 8 corresponds to FIG. 4.

Figure 9:
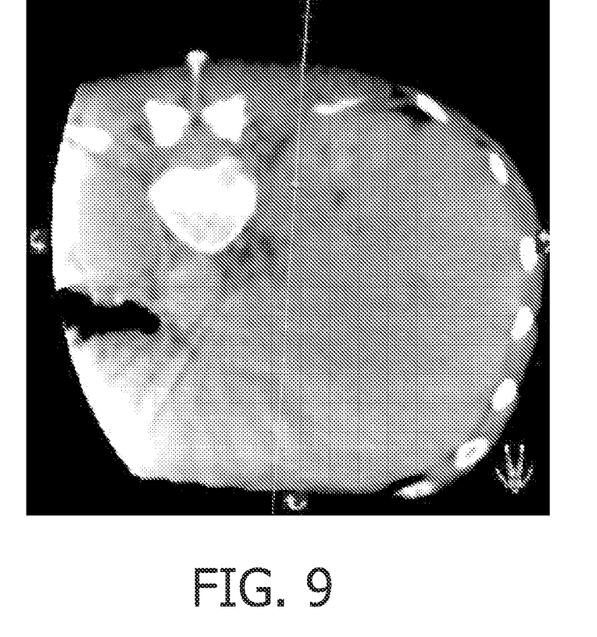
FIG. 9 shows the resulting cross sectional slice according to FIG. 8, in which a needle trajectory is to be planned.

In FIG. 9 the resulting cross sectional slice is shown, in which the needle trajectory is to be planned. In particular, FIG. 9 corresponds to FIG. 5. A graphical object in form of a small sphere indicates the target point as in FIGS. 7 and 8. Further a scale can be seen in FIG. 9 which is in coincidence to a path of approach. The scale can be used in order to determine the advancing of the needle on the planned path.

Figure 10:
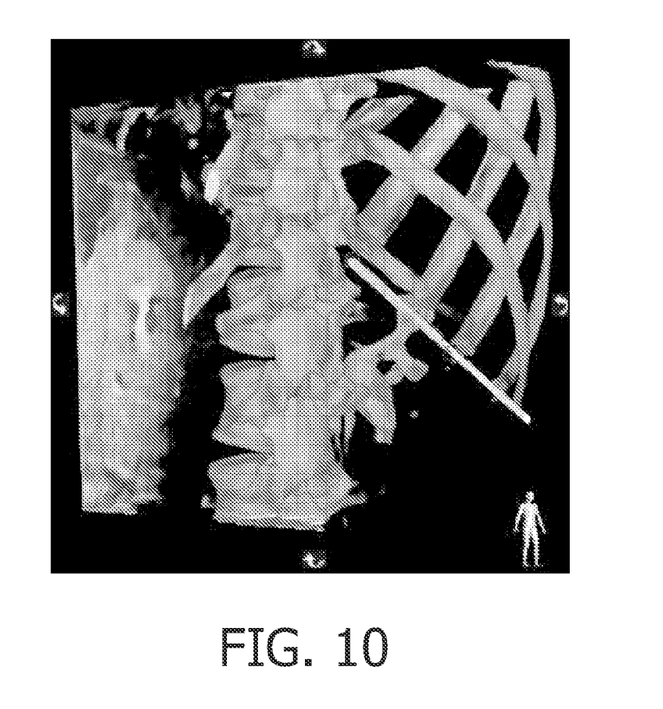
FIG. 10 shows the 3D volume of FIG. 8 that is acquired after needle insertion.

Finally, in FIG. 10 a 3D check up volume is shown that is acquired after needle insertion which shows the inserted needle in relation to the planned path. In particular, FIG. 10 corresponds to FIG. 6. The target point near the center of FIG. 10 is presented as a 3-D circle such as an entry point into the body of a patient near the image border. Generally, during 3D visualisation an orthographic projection is used.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention claimed is:

1. A method for targeting a first interventional object of a targeting device to a target point in an object under examination, the method comprising the following steps:

receiving in a processor of the targeting device a first two-dimensional image from an imaging device of a three-dimensional data volume representing the object under examination;

receiving in the processor a target point in the first two-dimensional image;

operating the processor to display an image of the three-dimensional data volume with the selected target point represented as a three-dimensional structure having a distance scale within its image, wherein the three-dimensional data volume is combined with a three-dimensional angiographic volume rendering of the same object under examination;

operating the processor to position the image of the three-dimensional data volume by scrolling and/or rotating about the target point center to make a path of approach crossing the target point having a first direction parallel to an actual viewing direction of the said image of the three-dimensional data volume;

operating the processor to generate a second two-dimensional image out of the three-dimensional data volume wherein a normal of the plane of the second two-dimensional image is oriented parallel to the first direction and crosses the target point;

operating the processor to render the image of the three-dimensional data volume, the three-dimensional structure having a distance scale within its image, and the two-dimensional image under the same perspective, wherein the imaging device is focused on an extension of the path of approach;

moving the first interventional object to target the target point in the object under examination according to the path of approach; wherein the path of approach avoids perforation of any vessel in the three-dimensional angiographic volume rendering.

2. The method according to claim 1, further comprising:
generating a third two-dimensional image out of the three-dimensional data volume, wherein the plane of the third two-dimensional image is oriented parallel to the first direction and crosses the target point.

3. The method according to claim 1, wherein the two-dimensional images are selected as slices of the three-dimensional data volume of the object under examination.

4. The method according to claim 1, wherein the first interventional object is a needle and the path of approach is the trajectory path of the needle through the object under examination.

5. The method according to claim 1, further comprising: determining an entry point of the path of approach into the object under examination.

6. The method according to claim 1, further comprising: projecting the entry point and/or the target point by a three-dimensional sphere in the three-dimensional data volume.

7. The method according to claim 1, wherein the path of approach is represented as a three-dimensional line.

8. The method according to claim 1, wherein the target point is represented as a three-dimensional sphere, circle or cross-hair in the three-dimensional data volume.

9. The method according to claim 1, wherein the first two-dimensional image is an cross-sectional view of the object under examination.

10. The method according to claim 1, wherein the selection of the third two-dimensional image is caused by manually clicking on the representation of the target point.

11. The method according to claim 1, further comprising: toggling between the third two-dimensional image and the second two-dimensional image and/or the image of the three-dimensional data volume.

12. The method according to claim 1, further comprising: displaying at least two of the said images to the user in a predefined orientation.

13. The method according to claim 1, wherein the object under examination is a patient; and wherein the predefined orientation of said images is an axial feet to head multi planar reformat (MPR) rendered cross section out of a 3D reconstructed data volume with no rotation angle around a perpendicular viewing direction of the plane of said images.

14. The method according to claim 1, further comprising regions of interest in the object under examination that are coloured.

15. The method according to claim 14, wherein at least portions of the coloured regions of interest in the object under examination and/or at least portions of the path of approach, the entry point, and the target point which extend apart from the plane of the third two-dimensional image are rendered semi-transparent.

16. The method according to claim 1, wherein the three-dimensional image is reconstructed out of the three-dimensional data volume recorded by a computer tomography apparatus.

17. The method according to claim 1, wherein the three-dimensional image is recorded by a C-arm device.

18. The method according to claim 1, further comprising: generating a 2D image showing the planned path and the target point and overlaying the 2D image on at least one of the two-dimensional images of the object under examination.

19. The method according to claim 1, further comprising projecting a scale on the path of approach in at least one of the two-dimensional images.

20. A device for targeting a first interventional object to a target point in an object under examination, the device comprising:
a processor that selects from an imaging device a first two-dimensional image of a three-dimensional data volume representing the object under examination, wherein the first two-dimensional image contains a target point;
a display that displays an image of the three-dimensional data volume with the target point;
wherein the processor positions the said image of the three-dimensional data volume by scrolling and/or rotating about the target point center to make a path of approach crossing the target point having a first direction parallel to an actual viewing direction of the said image of the three-dimensional data volume, wherein the processor represents the target point as a three-dimensional object having a distance scale within its image, and wherein the processor combines the three-dimensional data volume with a three-dimensional angiographic volume rendering of the same object under examination;
a generator that generates a second two-dimensional image out of the three-dimensional data volume, wherein a normal of the plane of the second two-dimensional image is oriented parallel to the first direction and crosses the target point;
wherein the processor renders the image of the three-dimensional data volume, the three-dimensional structure having a distance scale within its image, and the two-dimensional image under the same perspective, wherein the imaging device is focused on an extension of the path of approach;
a motor that moves the first interventional object to target the target point in the object under examination according to the path of approach; wherein the path of approach avoids perforation of any vessel in the three-dimensional angiographic volume rendering.

21. A system for targeting a first interventional object in an object under examination, the system comprising:
a radiation source;
a radiation detector; and
a device according claim 20, wherein the radiation detector records the data representing the three-dimensional data volume.

22. The system according to claim 21, further comprising: a computer tomography apparatus, wherein the computer tomography apparatus generates the two-dimensional images of the object under examination.

23. A tangible computer readable medium in which a program for targeting a first interventional object to a target point in an object under examination is stored as non-transitory computer data, the program comprising instructions configured to perform a method comprising the following steps:
receiving in a processor of the targeting device providing a first two-dimensional image from an imaging device of a three-dimensional data volume representing the object under examination;
determining a target point in the first two-dimensional image;
operating the processor to display displaying an image of the three-dimensional data volume with the selected target point represented as a three-dimensional structure having a distance scale within its image, wherein the three-dimensional data volume is combined with a three-dimensional angiographic volume rendering of the same object under examination;
operating the processor to position positioning the said image of the three-dimensional data volume by scrolling and/or rotating about the target point center to make a path of approach crossing the target point having a first direction parallel to an actual viewing direction of the said image of the three-dimensional data volume;
operating the processor to generate generating a second two-dimensional image out of the three-dimensional data volume wherein a normal of the plane of the second two-dimensional image is oriented parallel to the first direction and crosses the target point;

operating the processor to render the image of the three-dimensional data volume, the three-dimensional structure having a distance scale within its image, and the two-dimensional image under the same perspective, wherein the imaging device is focused on an extension of the path of approach;

moving the first interventional object to target the target point in the object under examination according to the path of approach; wherein the path of approach avoids perforation of any vessel in the three-dimensional angiographic volume rendering.

* * * * *